United States Patent [19]
Ripich et al.

[11] Patent Number: 5,916,228
[45] Date of Patent: Jun. 29, 1999

[54] TONGUE SCRAPER

[76] Inventors: Robert J. Ripich, 2622 Glenmont Rd., NW.; James Bower, 2810 Brentwood Close, NW., both of Canton, Ohio 44708

[21] Appl. No.: 08/940,146

[22] Filed: Sep. 29, 1997

[51] Int. Cl.[6] .................................................. A61B 17/22
[52] U.S. Cl. ............................................. 606/161; 15/111
[58] Field of Search ............................... 606/1, 160, 161; 15/111

[56] References Cited

U.S. PATENT DOCUMENTS

| | | |
|---|---|---|
| D. 264,878 | 6/1982 | Kitzis . |
| D. 265,506 | 7/1982 | Finamore . |
| D. 291,001 | 7/1987 | Gaskins . |
| D. 295,343 | 4/1988 | Regalado . |
| D. 295,695 | 5/1988 | Golzari . |
| D. 301,372 | 5/1989 | Tsen . |
| D. 303,426 | 9/1989 | Simonian . |
| D. 324,912 | 3/1992 | Hansen . |
| D. 360,262 | 7/1995 | Ly . |
| D. 365,395 | 12/1995 | Miyauchi . |
| D. 367,707 | 3/1996 | Baker . |
| 872,567 | 12/1907 | Langstaff ................................ 606/160 |
| 1,811,775 | 7/1931 | Barkwill ................................. 606/161 |
| 3,491,747 | 1/1970 | Robinson ................................ 606/160 |
| 4,455,704 | 6/1984 | Williams . |
| 4,488,327 | 12/1984 | Snider . |
| 4,582,059 | 4/1986 | Tiwari . |
| 4,875,496 | 10/1989 | Prabhudass . |
| 5,061,272 | 10/1991 | Reese . |
| 5,217,475 | 6/1993 | Kuber . |
| 5,226,197 | 7/1993 | Nack et al. . |
| 5,282,814 | 2/1994 | Srivastava . |
| 5,569,278 | 10/1996 | Persad . |

FOREIGN PATENT DOCUMENTS 0200258  8/1907  Germany ............................... 606/161

OTHER PUBLICATIONS

Ad for "OraFresh Tongue Cleaner", Jan. 1997.

Primary Examiner—Michael Buiz
Assistant Examiner—William Lewis
Attorney, Agent, or Firm—Sand & Sebolt

[57] ABSTRACT

An improved tongue scraper or oral hygiene tool is designed to most effectively and harmlessly remove plaque, tartar, bacteria, dead tissue, food debris, etc. from the tongue. The tool is made of a nonporous substance capable of withstanding high temperatures during repeated sterilization such as metal, and preferably stainless steel. The tool includes unique curves and smooth edges designed to define a working edge contoured similar to that of the tongue and having a nongagging and self-cleaning profile and size.

24 Claims, 7 Drawing Sheets

TONGUE SCRAPER

BACKGROUND OF THE INVENTION

1. Technical Field

The invention relates to tongue cleaning devices. More particularly, the invention relates to devices designed and used for removal of plaque, tartar, bacteria, food debris, and dead tissue from the tongue since buildup of plaque, tartar, bacteria, and food debris may result in halitosis or bad breath, tooth decay, and gum disease. Specifically, the invention is a reusable tongue scraping device of a unique design, shape and configuration so as to be reusably sterilizable, self-cleaning and easily rinsed, nongagging, tongue-fitting, and nonthreatening while effectively and harmlessly removing plaque, tartar, bacteria, food debris, dead tissue, and other microorganisms from the tongue thereby reducing or eliminating halitosis or bad breath, tooth decay, and gum and other periodontal diseases.

2. Background Information

It is well known that plague, tartar, bacteria, food debris, dead tissue, and other debris and microorganisms live and/or accumulate within the mouth and throat, including on the teeth and tongue. For this reason, most people brush their teeth one or more times per day so as to attempt to remove at least some of this particulate. In addition, it is also common practice for most people to floss between their teeth as well as gargle or rinse their mouth out with various mouth rinses and mouth washes for the same or similar reasons. Most individuals further regularly see a dentist or other oral/dental hygiene provider during which the teeth are cleaned, although this is generally accomplished no more often than twice per year. These basic forms of oral hygiene are widely accepted in the civilized world.

Furthermore, many people use gum, breath mints, and other products to freshen their mouth and thus their breath. These gum and mints are only short term ways of covering up the problem, that is the accumulation of the above-mentioned materials within the mouth, and therefore the above-mentioned processes of brushing and flossing are still required.

However, these processes of brushing and flossing teeth, as well as gargling and/or rinsing of the mouth with various rinses and mouth washes, are not always successful, or are sometimes only partially successful, in removing all of the plaque, tartar, bacteria, food debris, and dead tissue from the entire mouth cavity, and particularly the tongue since much of the focus is on the teeth. This focus by these well-known oral hygiene processes is well founded for tooth decay prevention, but is only a part of general mouth and throat hygiene since the buildup of plaque, tartar, bacteria, and food debris on the tongue may result in halitosis or bad breath, tooth decay, and gum disease. All of which have serious medical and/or social effects.

It has recently been discovered that halitosis or bad breath is a result of the buildup of the plaque, tartar, food debris, bacteria, dead tissue, and other microorganisms, either dead or alive, within the mouth cavity, and particularly on the tongue since the teeth are generally brushed regularly. In addition, it has been found that during sleep, the tongue often becomes coated with a film or coating having an offensive odor. Furthermore, during sleep and at other times of the day, saliva, mucus, sinus drainage, and other materials often dry on the tongue providing additional buildup. Finally, various bacteria and viruses also may buildup on the tongue when one is ill. All of this buildup is undesirable since the tongue, although generally smooth in nature, includes projections, grooves, and other minute crevices in which bacteria, germs, etc. can accumulate and grow causing mouth odors. Coupled with this is the transformation of the various buildup including these bacteria and germs as well as food debris, dead cells, and other microorganisms into plaque and tartar when mixed with saliva. It is well-known that this plaque is a source of offensive mouth odors. The soft, yet flexible nature of the tongue when coupled with the above-described uneven yet generally smooth terrain thereof, supplies the plaque with sufficient surface area to relatively permanently affix itself to, absent a scraping or similar removal process.

In the past, cleaning of the tongue has often been overlooked, or alternatively has been primitively attempted using the brushes on a conventional toothbrush. The toothbrush, however, is not well suited for this purpose since the bristles of the toothbrush are often too soft and flexible to remove the hard buildup described above. In addition, the overall size, shape and configuration of the toothbrush makes the toothbrush not well suited for the removal of this buildup from the tongue.

As a result, it was discovered that tongue cleaning devices specifically designed solely for use as tongue scrapers could possibly better clean off the above-mentioned buildup including the plaque, tartar, bacteria, food debris, and dead tissue that results in halitosis or bad breath, tooth decay, and gum disease. Prior examples of such tongue cleaning devices are shown in U.S. Pat. Nos. 4,445,704, 4,488,327, 4,582,059, 4,875,496, 5,061,272, 5,217,475, 5,226,197, 5,282,814, 5,569,278, as well as U.S. Design Pat. Nos. D242,744, D246,878, D265,506, D291,001, D295,343, D295,695, D301,372, D303,426, D324,912, D360,262, D365,395, and D367,707.

Although many of these prior art tongue cleaning devices were satisfactory for their intended purpose of cleaning at least some of the buildup from the tongue, several disadvantages or problems exist in the design and use of these, and therefore an improved tongue scraper design is needed. These disadvantages and problems include:

(1) an inability to sterilize the tongue scraper at all, repeatedly, or at sufficiently high temperatures such as those encountered in either professional disinfecting machinery or home dishwashers, due to the plastic or soft/thin metal construction of the tongue scraper;

(2) a porous finish in which germs, bacteria, microorganisms, and other microbial material may collect, breed, grow, etc.;

(3) a brittle or otherwise nondurable construction, such as plastic, which is not sufficiently tough and durable to withstand both use and misuse;

(4) a construction capable of being marred, scratched, dented, fractured, or otherwise physically damaged, particularly by rough handling, thereby making the tongue cleaning device ineffective;

(5) a nonrigid construction which bends or otherwise gives too much during use, and/or a construction such as of plastic that does not maintain its rigidity over time;

(6) a configuration that is not contoured similar to the shape of the tongue;

(7) a size that is not similar to the size of the tongue;

(8) a shape that is not similar to the shape of the tongue;

(9) a working edge that does not remain in contact with the tongue surface throughout the entire cleaning process;

(10) a design which causes gagging;

(11) a design with grooves, crevices, or other spots that promote buildup within the device which is undesirable;

(12) a design that prohibits proper rinsing of the device thereby promoting buildup on the device;

(13) a handle design that is not ergonomic;

(14) a handle that is not of sufficient strength and rigidity as is needed during the cleaning process;

(15) a design that does not provide access to the most posterior portion of the tongue where the greatest concentration of plaque buildup occurs;

(16) a working edge design that clogs;

(17) a working edge design that does not sufficiently penetrate the tongue papillae;

(18) a handle that does not fit within standard toothbrush holders;

(19) a working edge or other surface that is hazardous and/or threatening due to sharp edges;

(20) a design too flimsy resulting in a lack of control during use;

(21) a size, shape, and design that is too short thereby increasing the risk of accidental swallowing or lodgement within the throat;

(22) a design that includes moving joints, fasteners, or other needless constructions that provide for more difficult and less effective use, as well as a device that is more expensive, less reliable, and more susceptible to breakage; and

(23) a plastic construction that is susceptible to wear, cracking, gouging, etc.

SUMMARY OF THE INVENTION

These and other disadvantages and problems have resulted in the Applicant's realization that a new device is needed to address and solve some and/or all of the above disadvantages and problems. This new device encompasses the following and other objectives and advantages.

Objectives of the invention include providing an improved oral hygiene device.

Another objective of the invention is to provide an improved tongue cleaning device.

Another objective of the invention is to provide an improved tongue-scraping device.

Another objective of the invention is to provide such an improved oral-hygiene device, tongue cleaning device, and/or tongue scraper that is replete of the disadvantages of the prior art devices including those disadvantages listed above.

Another objective of the invention is to provide an oral hygiene device, tongue cleaner and/or tongue scraper for removing plaque, tartar, food debris, bacteria, etc. from the surface of the tongue, and more particularly from the plurality of grooves, crevices, and other contours within the tongue and off of the papillae of the tongue, specifically in and around the fungiform and filiform papillae toward the base or dorsal surface of the tongue.

Another objective of the invention is to provide an oral hygiene device, tongue cleaner, and/or tongue scraper for eliminating or reducing mouth odors caused by plaque and other material buildup on the tongue.

Another objective of the invention is to provide an oral hygiene device, tongue cleaner, and/or tongue scraper that improves the taste of food by removing plaque and other material buildup from the tongue, and specifically from the taste buds on the tongue surface.

Another objective of the invention is to provide an oral hygiene device, tongue cleaner, and/or tongue scraper having a unique size, shape, configuration and design so as to maintain maximum contact with the tongue surface during use.

Another objective of the invention is to provide an oral hygiene device, tongue cleaner, and/or tongue scraper having a configuration similar to the shape of the tongue, that is of a contour similar to the shape of the tongue.

Another objective of the invention is to provide an oral hygiene device, tongue cleaner, and/or tongue scraper having a size that is similar to the size of the tongue.

Another objective of the invention is to provide an oral hygiene device, tongue cleaner, and/or tongue scraper having a mouth insertion portion of a shape that is similar to the shape of the tongue.

Another objective of the invention is to provide an oral hygiene device, tongue cleaner, and/or tongue scraper having a working edge that remains in contact with the tongue surface throughout the cleaning process.

Another objective of the invention is to provide an oral hygiene device, tongue cleaner, and/or tongue scraper that is replete of grooves, crevices, or other spots that promote buildup of the scraped plaque, etc. within the device, which is undesirable.

Another objective of the invention is to provide an oral hygiene device, tongue cleaner, and/or tongue scraper that is designed to allow for rinsing of the device thereby eliminating buildup on the device.

Another objective of the invention is to provide an oral hygiene device, tongue cleaner, and/or tongue scraper that is designed to not include rivets, fasteners, or other joints and connectors that are susceptible to buildup of the scraped plaque, etc., and in the event of the breaking of the device could be swallowed or otherwise cause choking.

Another objective of the invention is to provide an oral hygiene device, tongue cleaner, and/or tongue scraper that is designed in a manner not too likely to elicit gagging, that is the gag reflex, during use which would preclude proper cleaning.

Another objective of the invention is to provide an oral hygiene device, tongue cleaner, and/or tongue scraper that is replete of sharp or otherwise tissue damaging edges or surfaces that could injure the tongue or other surfaces in the mouth or throat.

Another objective of the invention is to provide an oral hygiene device, tongue cleaner, and/or tongue scraper that is ergonomically or otherwise comfortably designed to fit the hand of a standard user.

Another objective of the invention is to provide an oral hygiene device, tongue cleaner, and/or tongue scraper that is constructed so as to be capable of repeated sterilization at very high temperatures such as those encountered in either professional disinfecting machinery or home dishwashers without any damage to the invention.

Another objective of the invention is to provide an oral hygiene device, tongue cleaner, and/or tongue scraper with a nonporous surface that is replete of pores in which germs, bacteria, microorganisms, and other microbial material may collect, breed, grow, etc.

Another objective of the invention is to provide an oral hygiene device, tongue cleaner, and/or tongue scraper of a durable construction that is sufficiently tough and durable to withstand both use and misuse.

Another objective of the invention is to provide an oral hygiene device, tongue cleaner, and/or tongue scraper of a construction resistant to marring, scratching, denting, fracturing, or otherwise physical damage, particularly by rough handling, since these surface or edge occlusions would make the tongue cleaning device ineffective.

Another objective of the invention is to provide an oral hygiene device, tongue cleaner, and/or tongue scraper of a rigid construction which resists bending yet is not so brittle as to break when a bending force is applied thereto.

Another objective of the invention is to provide an oral hygiene device, tongue cleaner, and/or tongue scraper having a handle design that is ergonomic.

Another objective of the invention is to provide an oral hygiene device, tongue cleaner, and/or tongue scraper having a handle that is of sufficient strength and rigidity as is needed during the cleaning process.

Another objective of the invention is to provide an oral hygiene device, tongue cleaner, and/or tongue scraper having a design that allows the user to gain access to the most posterior portion of the tongue where the greatest concentration of plaque buildup occurs.

Another objective of the invention is to provide an oral hygiene device, tongue cleaner, and/or tongue scraper having a working edge design that reduces or eliminates clogs.

Another objective of the invention is to provide an oral hygiene device, tongue cleaner, and/or tongue scraper having a working edge design that allows for sufficient penetration of the tongue papillae.

Another objective of the invention is to provide an oral hygiene device, tongue cleaner, and/or tongue scraper having a handle that fits within standard toothbrush holders.

Another objective of the invention is to provide an oral hygiene device, tongue cleaner, and/or tongue scraper having a working edge or other surface that is not hazardous and/or threatening due to sharp edges.

Another objective of the invention is to provide an oral hygiene device, tongue cleaner, and/or tongue scraper having a design of sufficient rigidity thereby providing sufficient control during use.

Another objective of the invention is to provide an oral hygiene device, tongue cleaner, and/or tongue scraper that is of a size, shape, and design that is long enough to decrease the risk of accidental swallowing or lodgement within the throat.

Another objective of the invention is to provide an oral hygiene device, tongue cleaner, and/or tongue scraper having a design replete of moving joints, fasteners, or other needless constructions, thus providing for easier and more effective use, as well as a device that is less expensive, more reliable, and less susceptible to breakage.

Another objective of the invention is to provide an oral hygiene device, tongue cleaner, and/or tongue scraper that is easily, effectively, and efficiently manufactured and marketed.

Another objective of the invention is to provide an oral hygiene device, tongue cleaner, and/or tongue scraper that is simplified and inexpensive to manufacture and market.

Another objective of the invention is to provide a tongue cleaning device that meets all of the above-mentioned objectives.

These and other objectives and advantages of the invention are achieved by the improved tongue scraper, the general nature of which may be stated as a unitary tongue scraper including a handle integrally attached to a body having a working surface.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION OF THE PREFERRED EMBODIMENTS

Figure 1:
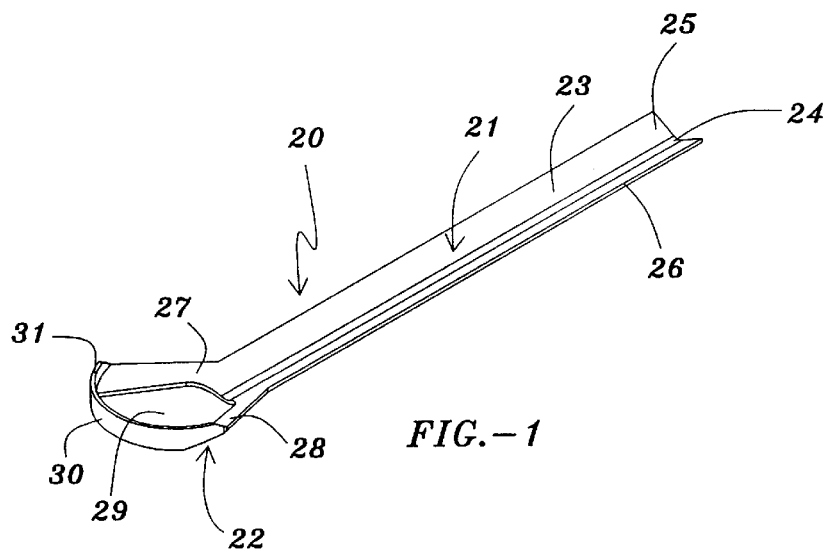
FIG. 1 is a perspective view of a first embodiment of the tongue scraper invention.
Figure 2:
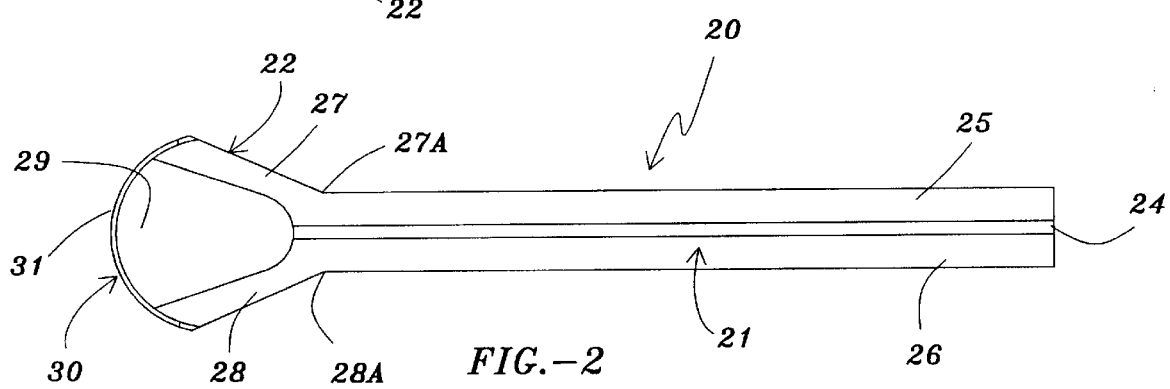
FIG. 2 is a top view of the tongue scraper of FIG. 1.
Figure 3:
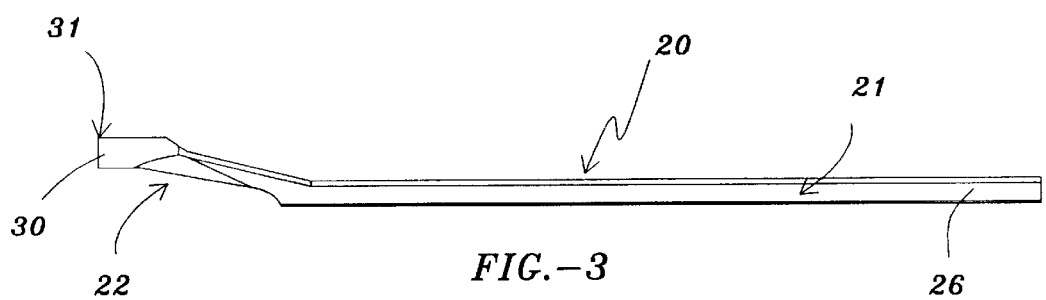
FIG. 3 is a side view of the tongue scraper of FIG. 1.

The improved tongue scraper is embodied in a number of different embodiments as shown in FIGS. 1–18. The first embodiment is shown in FIGS. 1–3 as a tongue scraper 20 including a handle 21 and a body 22. Handle 21 is an elongated structure 23 that is preferably V-shaped as is best shown in FIG. 1. This V-shape includes the valley base 24 and opposing sides 25 and 26, whereby the V-shape provides added strength as well as a rounded outside surface that fits within the user's hand and a valley 24 that is easy for the user to hold by inserting his/her thumb therein.

The handle 21 terminates by splitting in a "Y"-like manner into body 22. Specifically, body 22 includes a pair of legs 27 and 28 that each split off substantially longitudinally and in a substantially planar manner from its respective side 25 and 26 as is best shown in FIGS. 1 and 2. The body 22 via each of the legs is slightly angled obliquely from the handle as is best shown in FIG. 3 as the body 22 extends away from the handle 21. This angle is approximately 20° from the plane defined by the handle as is shown in FIG. 3, although this angle may vary slightly by approximately ±10° as needed.

This splitting defines a center hole 29 of a V-shape with a rounded base as is shown in FIG. 2. This center hole 29 is enclosed by a scraping surface 30 transversely extending in a curved manner between the distal ends of the legs 27 and 28. Specifically, the scraping surface 30, when in use, is substantially vertical, while the handle 21 and legs 27 and 28 are substantially horizontal. The outermost edge 31 of the scraping surface 30 is the actual scraping edge. This edge 31 is shown as a smooth edge in the FIGS. 1–3, although it may alternatively be of a jagged, toothed, serrated, grooved, notched, stepped, or otherwise patterned or uneven construction including triangular and square toothed designs.

One such specific configuration of the tongue scraper 20 includes a handle 21 of approximately 5 inches in length from its outermost or distal end to its innermost or proximate end at the split where the body starts, and approximately 4.3 inches from the distal end to where the legs begin expanding outward from the handle at points 27A and 28A. The handle 21 is also approximately 0.5 inch wide. As to the center hole 29, its diameter at its maximum point is preferably approximately 1 to 1.1 inches with the width of the entire body 22 at its maximum being preferably approximately 1.3 to 1.4 inches. The overall length of the tongue scraper 20 is approximately 6 to 6.2 inches. As to the angle that the opposing sides 25 and 26 are apart, it is preferably approximately 117° across the valley, although it may vary therefrom.

The center hole 29 may alternatively be a parabola with a focal point approximately 0.5 to 0.75 inch back from the outermost point of the scraping surface 30 whereby the total depth of the center hole is approximately 1.25 to 1.5 inches. The angle of the parabola is approximately 30°.

Figure 4:
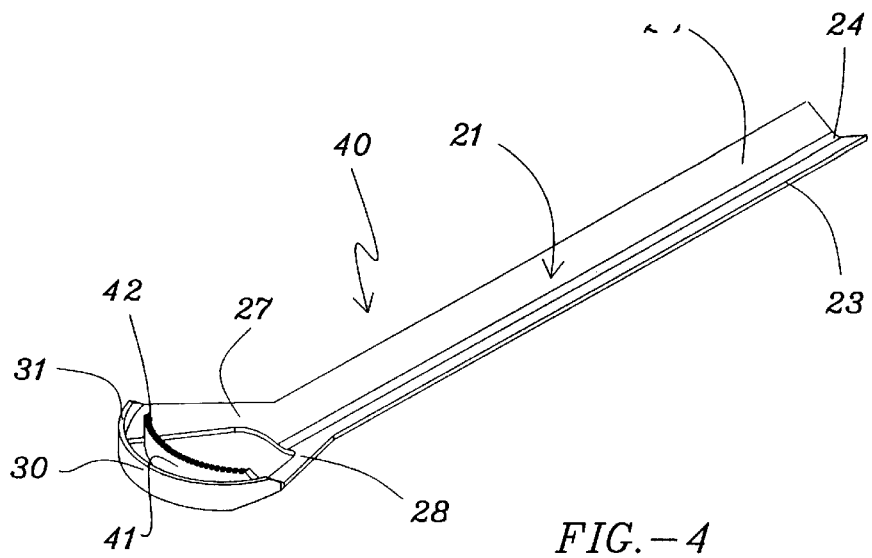
FIG. 4 is a perspective view of a second embodiment of the tongue scraper invention.
Figure 5:
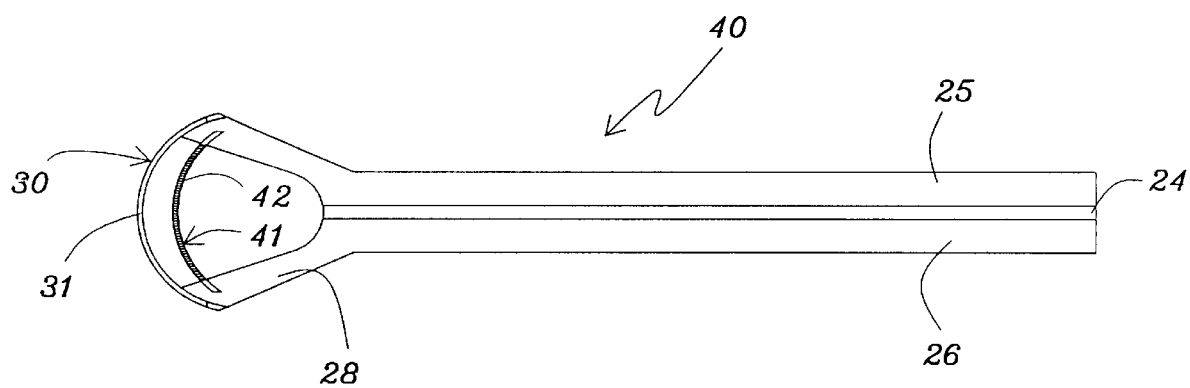
FIG. 5 is a top view of the tongue scraper of FIG. 4.
Figure 6:
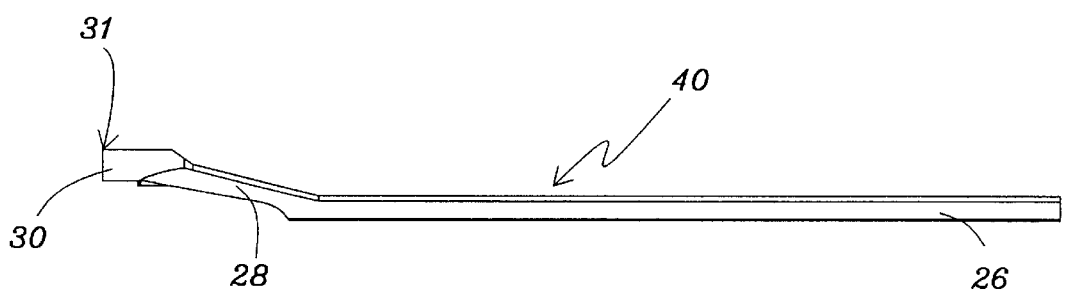
FIG. 6 is a side view of the tongue scraper of FIG. 4.

A second embodiment of a tongue scraper 40 is shown in FIGS. 4–6 of a substantially identical construction to the first embodiment of FIGS. 1–3 except that a second scraping surface 41 is provided as is shown. This second scraping surface 41 is similarly a transversely extending surface that is curved and extends between the legs 27 and 28 except at some mid-points rather than from the distal ends of the legs. The second scraping surface 41 includes an outermost edge 42 that is the scraping edge that is similarly of any of a number of constructions including serrated as shown in FIGS. 4–6, or alternatively smooth, jagged, toothed, grooved, notched, stepped, or otherwise patterned or uneven construction including triangular and square toothed designs.

In the case of either of the first two embodiments, the design is most effective for harmlessly removing plaque, bacteria, tartar, food debris, dead tissue, etc. which can cause halitosis, tooth decay, and gum disease. The tongue scrapers 20 and 40 are made of stainless steel that can be sterilized under intense heat in a repetitive nature without any damage to the device. The stainless steel has a nonporous finish so as to not allow organic material to collect on the device. The stainless steel construction allows the working edges 31 and 42 to remain unworn as each has exceptional durability over time and use. This working edge is further not easily marred by rough handling.

This design encompasses unique curves of the working edge that are designed to fit the muscle contours of the tongue most effectively as the tool is dragged with moderate pressure over the tongue surface. This is achieved through the semi-circular or approximately semi-circular shape of the front of the tool 20 or 40 and the profile of the curve on the material normal to the plane of this semi-circle.

This design further provides unequaled nongagging which is achieved through a combination of (1) the optimal depth-to-height ratio of the curve at the center of the working edge and (2) the slope or depth of the working edge in relation to where the handle begins.

The design is further a self-cleaning configuration that allows the working edge blade to be rinsed without the possibility of debris collecting in any corners.

The thickness of the working edge is optimized through the design of the tools 20 and 40 using 22 gauge stainless steel which provides for this optimal working edge of approximately 0.03 inch (0.029 inch).

The design is further such that the handle length and angle are optimal for the fit of the natural contours of the thumb and palm of the hand while providing the optimal length to reach the most posterior regions of the tongue. The handle angle is also designed to provide the strength needed to support the working edge blade while maintaining a non-gagging contour. The handle 21 also is of a size, shape and design that fits in most toothbrush holders.

The unique angle of the tools 20 and 40 and the rounded corners and edges allows for optimal cleaning of the most posterior portion of the tongue which contains the greatest concentration of filiform papillae and associated plaque buildup.

The working edge is designed, no matter if serrated, jagged, toothed, grooved, notched, stepped, or otherwise patterned or uneven construction including triangular and square toothed designs, such that the grooves, ridges, or valleys are anti-clogging so as to allow for deeper penetration of the tongue papillae.

The working edge length via its curved geometry is maximized due to the optimal working edge blade depth-to-height ratio and tool head width being integrated. The tools 20 and 40 thus have more working edge per standard tool head width than the prior art tools which have a flat edge.

The stainless steel construction provides a rigid tool that is not flimsy, bendable, or otherwise flexible during use under pressure against the user's tongue.

The design further lacks joints, fasteners, bulky welds, etc., which define small or large crevices, grooves, etc. in which debris can collect.

Figure 7:
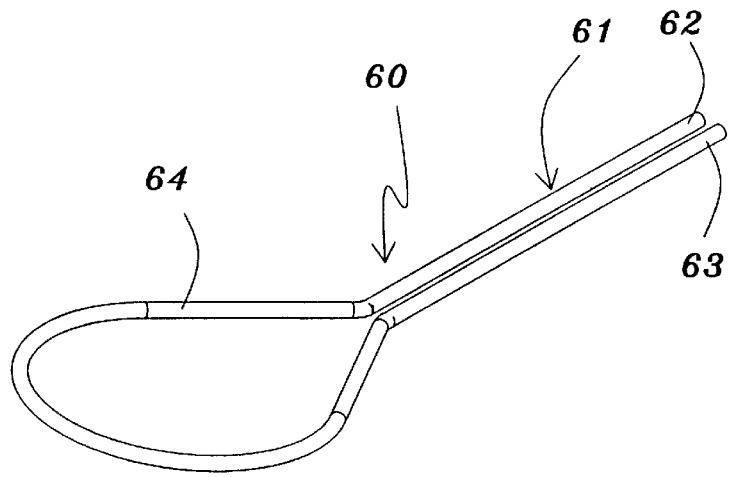
FIG. 7 is a perspective view of a third embodiment of the tongue scraper invention.
Figure 8:
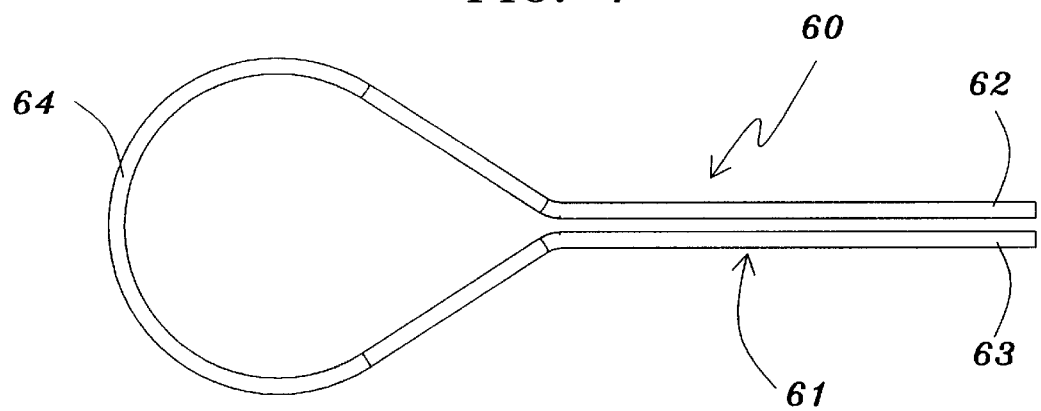
FIG. 8 is a top view of the tongue scraper of FIG. 7.
Figure 9:
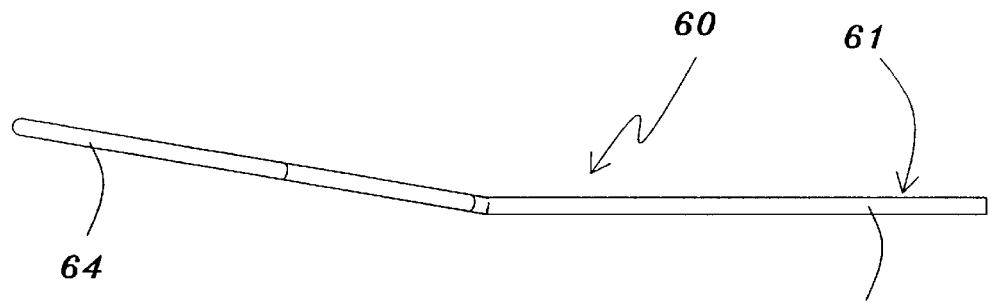
FIG. 9 is a side view of the tongue scraper of FIG. 7.

Additional alternative embodiments are shown in FIGS. 7–15 which include some or all of the above-described benefits. One such design is shown in FIGS. 7–9 where the tool 60 is a one-piece round rod bent into the configuration shown in the Figures. The tool is thus of a continuous smooth contour since in cross section it is circular. Basically, the tool design is a handle 61 including the two ends of the rod 62 and 63, and a tear-dropped or approximately circular-shaped body 64 comprising the mid-section of the rod. The body 64 is angled out of plane with the handle 61 as is shown in FIG. 9. The body 64 includes a rounded working edge 65.

Figure 10:
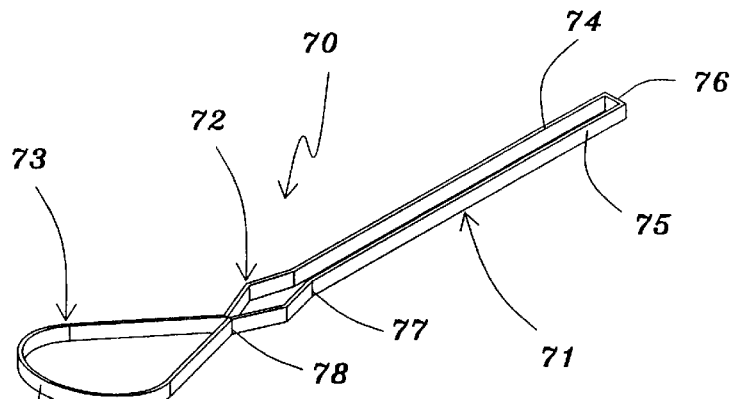
FIG. 10 is a perspective view of a fourth embodiment of the tongue scraper invention.
Figure 11:
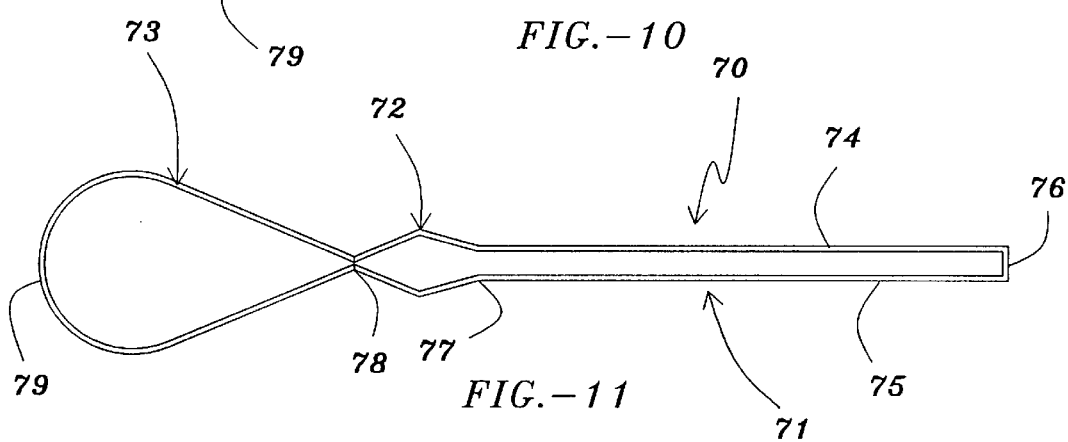
FIG. 11 is a top view of the tongue scraper of FIG. 10.
Figure 12:
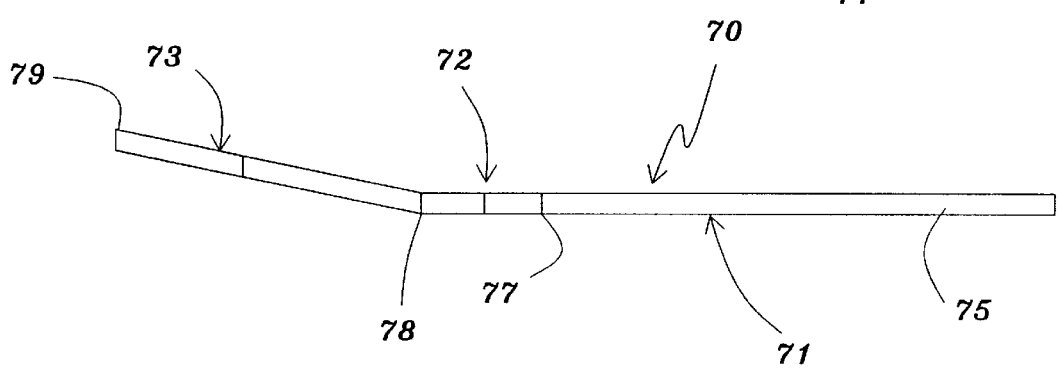
FIG. 12 is a side view of the tongue scraper of FIG. 10.

A second such design is shown in FIGS. 10–12 as tool 70. Tool 70 is a flat metal strip that is bent as is shown in the FIGS. 10–12 and connected smoothly at some point along the structure so as to be made out of only one piece. Tool 70 basically includes a handle 71, a neck 72, and a body 73. The handle 71 includes a pair of spaced apart yet parallel sections 74 and 75 connected at a distal end 76 by a short leg. The proximate ends 77 of the sections 74 and 75 extend into neck 72 which is of a general diamond shape with the opposing ends 78 almost touching. The body 73 is of a tear-drop or approximately circular shape and includes a working edge 79. The body 73 is again angled out of plane with the handle 71 and neck 72 as is shown in FIG. 12.

Figure 13:
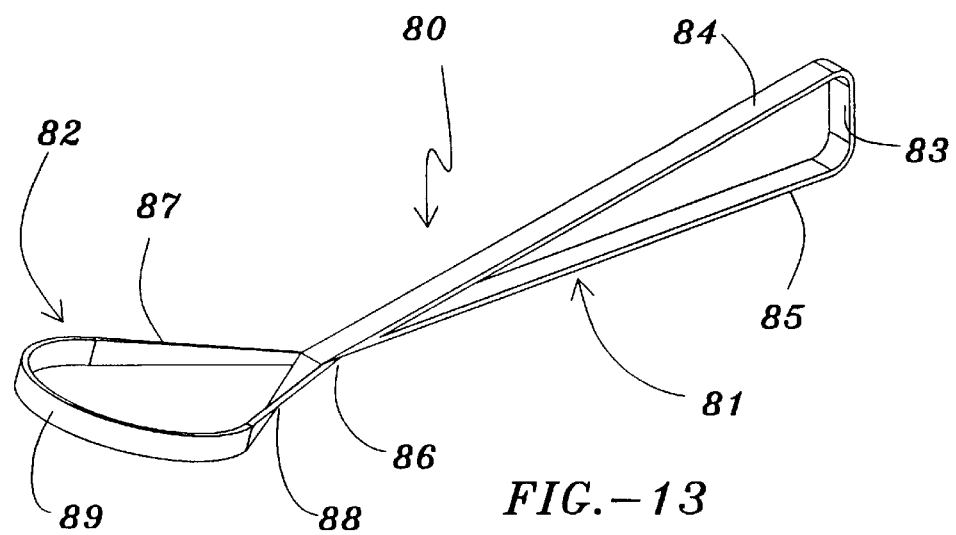
FIG. 13 is a perspective view of a fifth embodiment of the tongue scraper invention.
Figure 14:
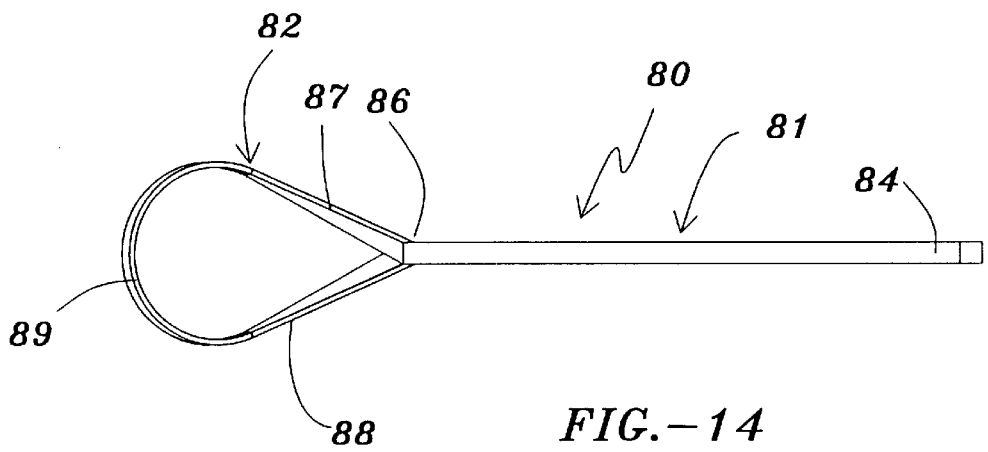
FIG. 14 is a top view of the tongue scraper of FIG. 13.
Figure 15:
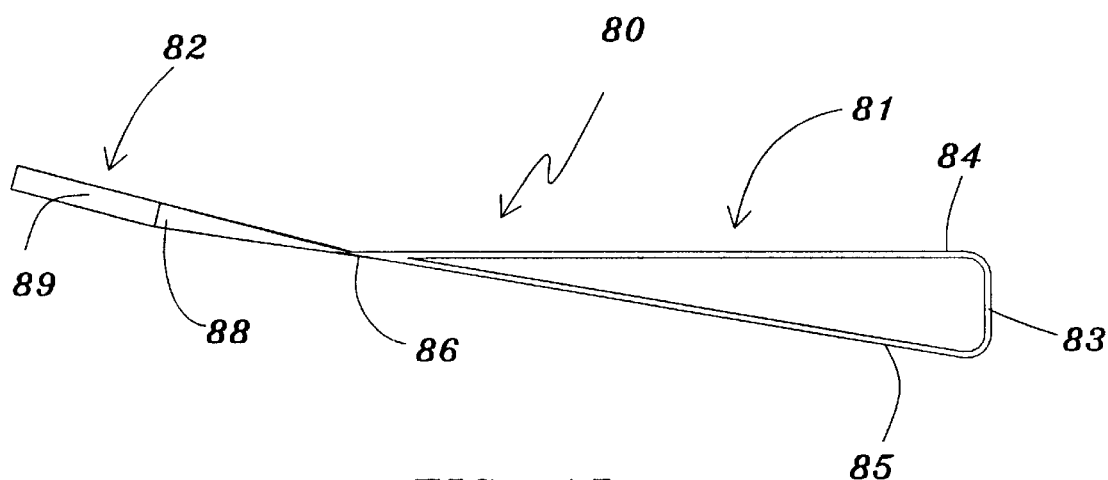
FIG. 15 is a side view of the tongue scraper of FIG. 13.

A third such design is shown in FIGS. 13–15 as tool 80. Tool 80 is similarly made of a flat metal strip. This strip is bent, twisted and/or otherwise configured as shown in FIGS. 13–15 and connected at some point along the structure so as to be made out of only one piece. Tool 80 basically includes a handle 81 and a body 82. Handle 81 is of an elongated triangular shape having a short end 83 and a pair of opposing yet converging sides 84 and 85. After each of the sides 84 and 85 converge at point 86, these sides are twisted approximately 90° as best shown in FIG. 13 and directed divergently away to form tear-drop or approximately circular shaped body 82. This body 82 includes a pair of diverging sides 87 and 88 and a curved end 89 that is the working edge. The section of flat metal strip in working edge 88 is substantially perpendicular to the section of flat metal strip in handle 81. A weld may be used to hold the sides 84 and 85 together at point 86 and through the twist. The body 82 is out of plane with one side 84 of the handle while either in plane or close to in plane with the other side 85 as is best shown in FIG. 15.

Figure 16:
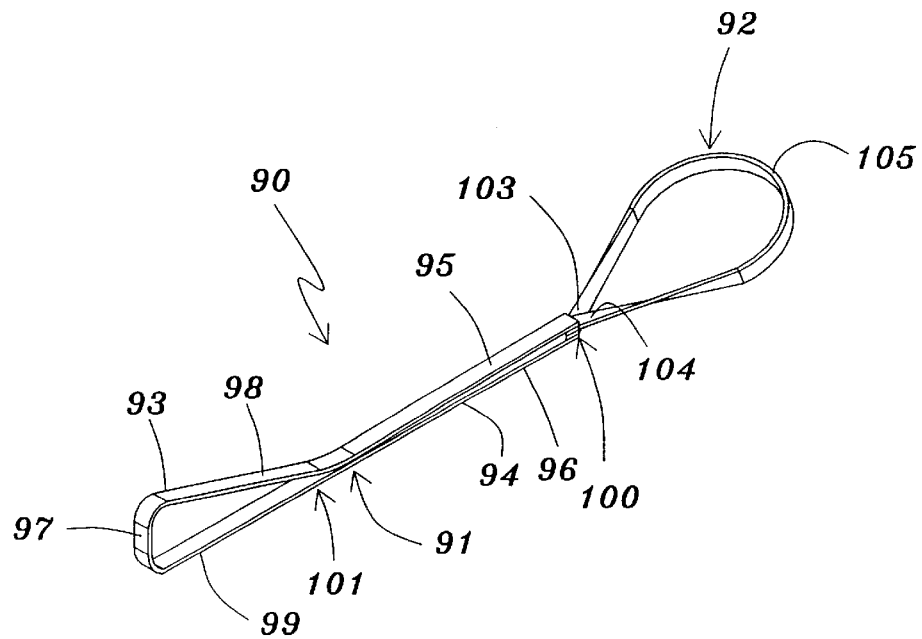
FIG. 16 is a perspective view of a sixth and final embodiment of the tongue scraper invention.
Figure 17:
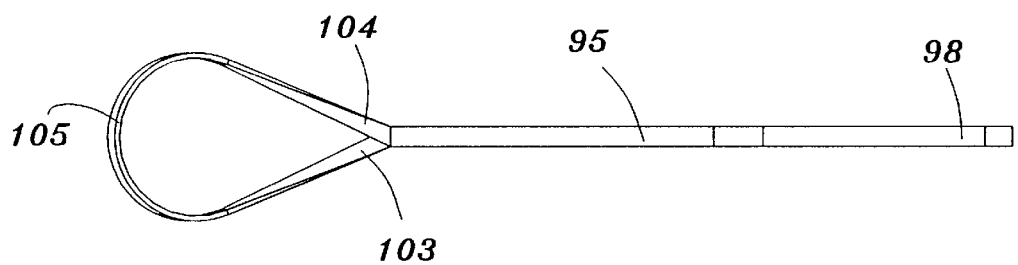
FIG. 17 is a top view of the tongue scraper of FIG. 16.
Figure 18:
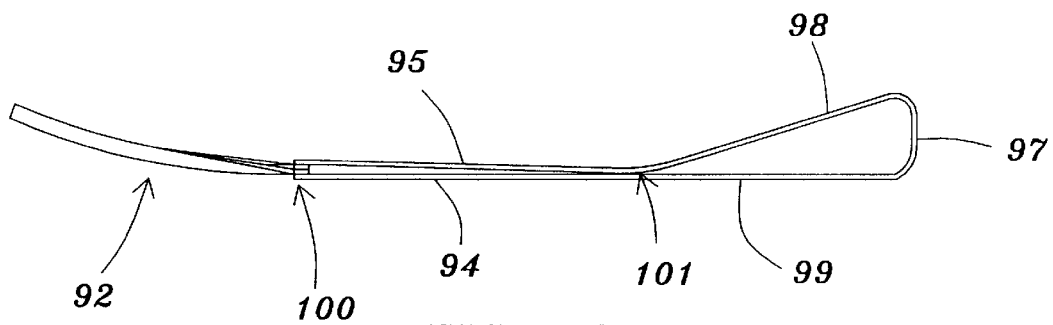
FIG. 18 is a side view of the tongue scraper of FIG. 16.

A fourth such design is shown in FIGS. 16–18 as tool 90. Tool 90 has some similarities to tool 80 as described above. Tool 90 is made of two flat metal strips 91 and 92 whereby each strip is bent, twisted and/or otherwise configured as shown in FIGS. 16–18 into tongue scraping tool 90. Configured flat metal strip 91 is principally the handle, while configured flat metal strip 92 is principally the body.

Handle 91 includes a triangular, distal portion 93 and a generally flat, proximate portion 94. Specifically, handle 91 is bent and/or otherwise configured into the shape as most clearly shown in FIG. 18 to include first and second planar spans 95 and 96 making up the generally flat portion 94, and a short end 97 and first and second converging sides 98 and 99 making up the triangular portion 93. In assembly, spans 95 and 96 extend in a substantially or somewhat parallel manner away from a connection point 100 in the same direction. The spans 95 and 96 merge or join together at a contact point 101 whereafter the spans diverge apart as sides 98 and 99 (which converged at point 101) toward short end 97. Each side 98 and 99 bends up to 90° into short end 97. Thus, handle 91 includes an ergonomic, easy-to-hold portion 93 and an extension portion 94 of minimal yet sufficiently strong substance from the easy-to-hold portion to the connection point 100 with the body 92.

Body 92 is an elongated piece of flat metal twisted such that a first end 103 touches and is parallel to a second end 104 of the body 92 while the mid-section 105 therebetween is transversely situated as shown in FIGS. 16–18. Specifically, the inner and outer face of mid-section 105 is angled at between 45° and 90° of the plane of the inner and outer faces of ends 103 and 104, and preferably at approximately 70° (although the strip has been twisted approximately 90° but the below described tilting accounts for the "net effect" 70° angle). In addition to the twisting as best shown in FIGS. 16 and 17 of body 92 from end 103 to mid-section 105 and back to end 104, body 92 also is curved or tilted in mid-section 105 as best shown in FIG. 18.

Figure 19:
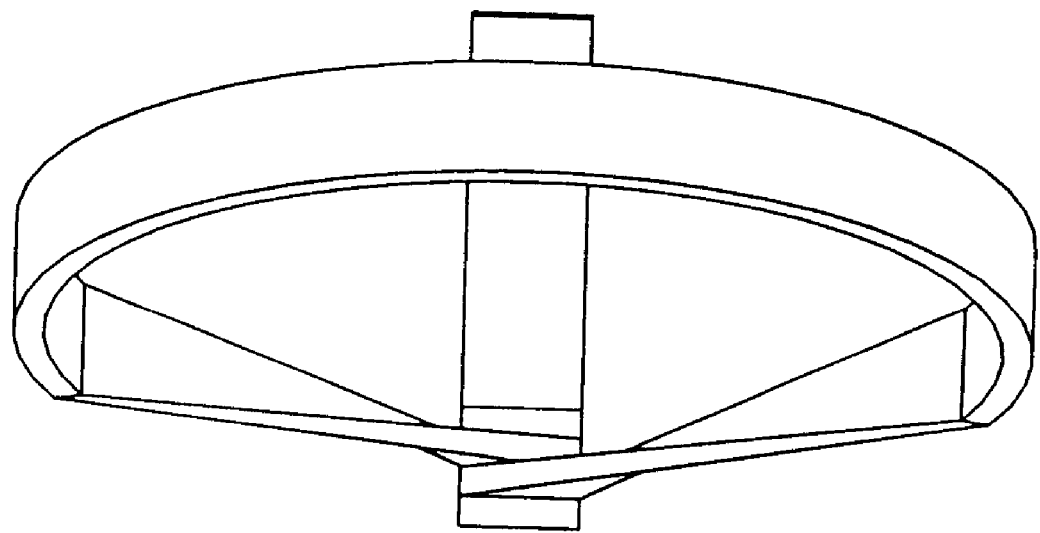
FIG. 19 is an end view of the tongue scraper of FIG. 16.

The ends of spans 95 and 96 sandwich ends 103 and 104 therebetween as best shown in FIGS. 19 and 21. All of these ends are then adhered together in any of a number of ways such as welding or adhesive bonding at connection point 100. In addition, preferably all of the sharp corners have previously been or now are rounded off. Similarly, the lengthwise edges on the metal strips 91 and 92 may be beveled, particularly the nonworking edges, so as to eliminate any sharp areas.

The contact point 101 is often welded or bonded also. If this is done, the spans 95 and 96 are no longer parallel and are instead substantially or somewhat parallel since a very thin triangle is in effect created as is shown in FIG. 21 between spans 95 and 96, and connection point 100.

In more detail, this fourth such design as shown in FIGS. 16–18 as tool 90 is constructed out of 22 gauge, ½ hard steel rolls. A smooth slitting process defines the width of the flat metal strips 91 and 92 from the large steel rolls. The smooth slitting process allows the steel to be cut without producing a sharp and therefore dangerous edge. Thereafter, each of the flat metal strips is inserted into a separate jig and bent into the shape as shown in FIGS. 16–18. Specifically, as to the body 92, a flat metal strip is inserted into a jig at its center and then bent 180 degrees at each end around the die so as to form the teardrop shaped body with the "net effect" 70 degree angled midsection 105 and the flat overlapping ends 103 and 104. The ends are then welded together. The handle is similarly bend around a die to form it into the elongated triangular shape as shown in FIGS. 16–18 which gives the handle design some flex and tension thereby providing sufficient rigidity to keep the working surface on the tongue during tongue scraping while giving it sufficient flex to allow it to give or bend during such use to avoid actual damage to the tissue. The handle and body are welded together to form the tool 90 as shown in FIGS. 16–18.

In one embodiment, the tool 90 prior to the welding of the two pieces of the body and handle together, but after the bending of each piece, is polished. Specifically, the polishing involves tumbling the metal pieces so as to further smooth the surfaces and edges. The tumbling could occur before the bending.

In another alternative embodiment, the entire tool 90 is coated using a powder coating technology. Once such possible powder coating is an epoxy resin, but others are equally applicable. Alternatively, the entire tool 90 could be dipped in a powder fluid resulting in a vinyl coating. It has also been found that multiple coatings can be placed on the tool 90 such as a first epoxy coat followed by a second vinyl coat. Various coated embodiments exist in that the entire tool 90 can be coated in either an epoxy resin or a vinyl coat, or multiple coats of one or both. In addition, only portions of the tool 90 such as only the handle or only the handle and a portion of the body (excluding for instance the working edge) could be coated while the remaining steel is left bare. Alternatively, the handle portion could be coated with a first type of coating while the body portion is coated with a second type of coating. Where portions are to be left uncoated, the preferred technique is to mask the edge with a masking tape or a masking chemical which can be later removed after coating.

Another possible design change is to the handle whereby the handle can be a right triangular shape as shown in FIGS. 13–15 or the preferred modified triangle with a flat portion as shown in FIGS. 16–18. As to the modified handle design, the handle at point 101 may be welded such that the upper section and lower section are attached or they may just touch at that point thereby providing additional flexibility to the handle. The handle could also be made stiffer by filling in the handle between portions 94 and 95 with either metal or some other material.

This embodiment has the following benefits, advantages, objectives, design features, and other attributes:

- Made of surgical quality stainless steel, which will not fracture.
- Stainless steel will give the entire tool and its working edge an exceptional durability not found in other plastic cleaning tools. In particular, the working edge is not easily marred by rough handling, a potentially hazardous problem associated with plastic tongue cleaning tools.
- Stainless steel material allows tool to maintain functionally rigid properties indefinitely.

Properties of stainless steel allow for unlimited sterilization cycles.

Can be sterilized using a dishwasher or other professional disinfecting machinery.

Nonporous finish does not allow organic material to collect on surface.

Unique curves comprising the working edge designed to fit the muscle contours of the tongue most effectively as the tool is dragged with moderate pressure over its surface.

Unique dual sided working "blade"—working edge shown in (A) designed to focus cleaning on central portion of tongue, and working edge (B) designed to focus cleaning on sides of tongue.

Working edge (A) designed to be obtuse, or greater than 90 degrees to tongue surface, so debris can be lifted away during cleaning process.

Unequaled "nongagging" design achieved through an optimal depth/height of the curve at the center of the working (C) and the slope or "depth" of the working edge in relation to where the handle begins.

A "self-cleaning" design allows for the working edge blade to be rinsed without the possibility of debris collecting in corners.

Properties of tool design and construction materials lend themselves to a variety of working blade angles and curves. Thus, there is the ability to create an infinite amount of scale models for different oral hygiene cases (i.e. small/large mouths, nonsensitive/sensitive tongues).

Designed to be tailored for every possible customer.

Unique curve of metal strip provides a progressive pressure spectrum from the middle of blade (C) toward the outer edges for cleaning the center of tongue using edge (A) or sides of tongue using edge (B). Unique design of tool allows for infinite incremental changes of this pressure spectrum through changes in the severity of blade curve during construction.

Ranges:

Width of strip: 0.150–0.166 inches.

Thickness of strip: 0.026–0.035 inches

Width of working blade (outside measurement, (D): 0.750–1.300 inches.

Depth/height of working blade (E): 0.100–0.500 inches.

Much lighter weight design as compared to any other stainless steel cleaners.

Designed for easy one-handed use as compared to older two-handed designs.

Two resistance type welds give handle and working blade optimal torsional strength and rigidity, yet in a very lightweight design.

Thickness of working edge optimized through use of 22-gauge steel (~0.029 in.)

Handle length and angle designed especially to fit the natural contours of the thumb and palm of the hand while providing the optimal length to reach the most posterior regions of the tongue where most bacteria are found.

The handle angle is also designed to provide the strength needed to support the working edge blade while maintaining superb "nongagging" contours.

Tool design allows cleaning of most posterior portion of tongue that contains greatest concentration of filiform papillae and associated plaque buildup.

The addition of specially designed, anti-clogging ridges on the working edge allows for deeper penetration of the tongue papillae.

Handle designed to fit into most toothbrush holders.

Sleek, aerodynamic design aids in the perception of Tongue Sweeper as a nonthreatening tool as opposed to other razor shaped, bulky designs.

Designed to be psychologically comforting by resembling common eating utensils.

Working edge length (its curve geometry) is maximized when the optimal working edge blade height/depth (E) and tool head width (D) are integrated. Thus, functionally, the Tongue Sweeper tool has more working edge than one which has a "flat" edge with the same tool head width.

The use of this unique tool reduces halitosis by decreasing the amount of plaque and organic food substrate that accumulates in and around fungiform and filiform papillae of the tongue. This reduces bacteria and sulphur byproducts that can cause halitosis, tooth decay, and gum disease.

Unique cleaning action of this tool on taste papillae results in improved taste sensation.

Completely rigid design allows complete control of tool in desired areas of tongue. This feature is not found in flimsy, plastic tongue cleaners.

The length of the tool and its inherent rigid properties make the Tongue Sweeper substantially less likely to be swallowed or inhaled than other short, flimsy products.

When the tool is coated, it provides an even smoother feel with a soft touch.

When the tool is coated, it removes all welds, corners, etc. from exposure.

When the tool is partially coated, it provides the coating advantages but still supplies the steel working edge and its advantages.

When the tool is coated, it still retains all of its flexibility properties and the high temperature sterilization safeness.

Accordingly, the improved tongue scrapers are simplified, provide effective, safe, inexpensive, and efficient devices which achieves all the enumerated objectives, provide for eliminating difficulties encountered with prior devices, and solve problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved tongue scrapers are constructed and used, the characteristics of the construction, and the advantageous, new and useful results obtained; the new and useful structures, devices, elements, arrangements, parts and combinations, are set forth in the appended claims.

We claim:

1. A tongue scraper comprising:

a handle having a generally planar lower length connected by at least one bend to an upper length planar at least in part with the lower length, and the handle having a pair of handle ends; and a body including at least one working surface for scraping a tongue when dragged thereacross, a body having a pair of adjacent and parallel body ends separated by a twisted mid-section that it transverse with the pair of body ends, and the pair of body ends being connected with the pair of handle ends.

2. The tongue scraper of claim 1 wherein the body is of a tear-drop shaped.

3. The tongue scraper of claim 1 wherein the mid-section is twisted approximately at least 90° from either end.

4. The tongue scraper of claim 1 wherein the mid-section is further tilted out of the plane defined by the generally planar lower length as the mid-section extends away from the body ends.

5. The tongue scraper of claim 4 wherein the mid-section is tilted approximately 20° out of the plane defined by the generally planar lower length.

6. The tongue scraper of claim 4 wherein the mid-section is between 0.1 and 0.5 inches away from the plane defined by the generally planar lower length.

7. The tongue scraper of claim 1 wherein the handle and body are made of stainless steel.

8. The tongue scraper of claim 1 wherein the width across of the handle and body is between 0.15 and 0.166 inches.

9. The tongue scraper of claim 1 wherein the thickness of the handle and body is between 0.026 and 0.035 inches.

10. The tongue scraper of claim 1 wherein the overall width of the body is between 0.75 and 1.3 inches.

11. The tongue scraper of claim 1 wherein the handle comprises the generally planar lower length connected by a short leg with a bend on each end to the upper length sloping in part and planar in part with said lower length.

12. The tongue scraper of claim 11 wherein the handle further includes a pair of handle ends at opposing ends of the handle and adjacent one another and slightly spaced apart.

13. The tongue scraper of claim 12 wherein said upper and lower lengths are connected at an apex in the upper length between said sloping part and said planar part.

14. The tongue scraper of claim 1 wherein the handle further includes a pair of handle ends at opposing ends of the handle and adjacent one another and slightly spaced apart.

15. A unitary tongue scraper comprising:

a handle of a generally planar construction and including a single elongated structure; the handle being of a V-shaped cross section including a valley separated by a pair of opposing sides extending upwardly from the valley; and a body including at least one working surface for scraping a tongue when dragged thereacross, and the body being of a generally planar construction that is not parallel with the planar construction of the handle;

the body including a pair of legs splitting from the handle to define a center hole formed in a parabolic shape between the pair of legs, whereby the working surface extends in a curved manner from the ends of the respective legs where the curve is defined as being equidistant from a focal point of the parabola.

16. The unitary tongue scraper of claim 15 wherein the angle the opposing sides are separated by is between approximately 100° and 140° across the valley.

17. The unitary tongue scraper of claim 16 wherein the angle is 117°.

18. The unitary tongue scraper of claim 15 wherein the body is between approximately 10° and 40° out of plane with the handle.

19. The unitary tongue scraper of claim 18 wherein the body is approximately 20° out of plane with the handle.

20. The unitary tongue scraper of claim 15 further comprising a second working surface spaced apart yet similarly shaped to the working surface.

21. The unitary tongue scraper of claim 15 wherein the body and handle are made of a nonporous, rigid, and fracture resistant material.

22. The unitary tongue scraper of claim 21 wherein the nonporous, rigid, and fracture resistant material is stainless steel.

23. The unitary tongue scraper of claim 15 wherein the body is between 0.1 and 0.3 inches high and between 1.3 and 1.4 inches wide.

24. The unitary tongue scraper of claim 15 wherein the handle includes a pair of sides that converge at a connection point with the body where a pair of legs on the body simultaneously converge whereby each of the sides turns into one of the legs as the side twists through the connection point.

* * * * *